(12) United States Patent
Liu

(10) Patent No.: US 10,624,331 B2
(45) Date of Patent: Apr. 21, 2020

(54) MOUSE REPELLER

(71) Applicant: Yu-Chen Liu, Guangdong (CN)

(72) Inventor: Yu-Chen Liu, Guangdong (CN)

(73) Assignee: Handle Tech (SZ) Co., Ltd., Shenzhen (CN)

( * ) Notice: Subject to any disclaimer, the term of this patent is extended or adjusted under 35 U.S.C. 154(b) by 332 days.

(21) Appl. No.: 15/866,530

(22) Filed: Jan. 10, 2018

(65) Prior Publication Data

US 2018/0125059 A1 May 10, 2018

(30) Foreign Application Priority Data

Sep. 29, 2017 (CN) ..................... 2017 2 1272938 U

(51) Int. Cl.
| | |
|---|---|
| *A01M 29/16* | (2011.01) |
| *A61L 9/22* | (2006.01) |
| *H01T 23/00* | (2006.01) |
| *H04B 1/04* | (2006.01) |

(52) U.S. Cl.
CPC ............. *A01M 29/16* (2013.01); *A61L 9/22* (2013.01); *H01T 23/00* (2013.01); *H04B 1/04* (2013.01); *H04B 2001/0408* (2013.01)

(58) Field of Classification Search
CPC . A01M 29/16; H04B 1/04; H04B 2001/0408; H01T 23/00; A61L 9/22
See application file for complete search history.

(56) References Cited

U.S. PATENT DOCUMENTS

2018/0125059 A1* 5/2018 Liu .................... A01M 29/16

FOREIGN PATENT DOCUMENTS

CN 207266578 U * 4/2018 ............ A01M 29/16

* cited by examiner

*Primary Examiner* — Daniel Pihulic

(57) ABSTRACT

The invention relates to a novel mouse repeller including a cavity defined by a shell and a base, and a power rectification and supply part, an ultrasonic output module and a negative ion generator which are located in the cavity, wherein the power rectification and supply part supplies power to the ultrasonic output module and the negative ion generator, the ultrasonic output module includes an ultrasonic transducer protruding out of the shell, and the negative iron generator includes a discharge electrode plate which is a detachable and cleanable electrode plate. The novel mouse repeller is of an integrated structure and has a remarkable mouse repelling effect; meanwhile, the adopted detachable and cleanable electrode plate is high in power and can be reused after being detached and cleaned, so that a powerful negative ion emitting effect is maintained, and the use cost is obviously reduced.

8 Claims, 3 Drawing Sheets

MOUSE REPELLER

BACKGROUND OF THE INVENTION

Technical Field

The invention relates to a mouse repelling device, in particular, to a novel mouse repeller.

Description of Related Art

Ultrasonic mouse repelling refers to powerful high-power high-frequency ultrasonic waves within the audibility range, 200 HZ-90000 HZ, of mice that are emitted to disturb and irritate the auditory systems of mice, so that the mice are made to flee the effective ultrasonic radiation range, and accordingly, the mice are repelled, and the activity space of the mice is limited. Based on the characteristic that mice like putrid smells, a negative ion generator can eliminate odors and refresh the air, the mice do not like the fresh environment, and thus an auxiliary mouse repelling effect can be achieved.

Ultrasonic mouse repellers on the present market only have the ultrasonic mouse repelling function, and the mouse repelling effect is limited. Or an ultrasonic mouse repeller and a negative ion generator are used at the same time, however, the cost is high, and the space of two sockets is required; meanwhile, the negative ion generator is a simple carbon brush type negative ion generator and extremely short in service life, the air purification effect is limited, and the mouse repelling effect is common.

BRIEF SUMMARY OF THE INVENTION

To overcome the defect that the mouse repelling effect of an ultrasonic mouse repeller and a negative ion generator in the prior art is average, the invention provides a novel mouse repeller.

According to the technical scheme adopted by the invention for solving the technical problems: a novel mouse repeller comprises a cavity defined by a shell and a base, and a power rectification and supply part, an ultrasonic output module and a negative ion generator which are located in the cavity, wherein the power rectification and supply part supplies power to the ultrasonic output module and the negative ion generator, the ultrasonic output module comprises an ultrasonic transducer protruding out of the shell, and the negative iron generator comprises a discharge electrode plate which is a detachable and cleanable electrode plate.

According to the novel mouse repeller of the invention, the shell is provided with a hole at the end of the discharge electrode plate, and the shape of the hole is matched with the shape of the end face of the discharge electrode plate.

According to the novel mouse repeller of the invention, the discharge electrode plate is a negative ion static electrode.

According to the novel mouse repeller of the invention, the power rectification and supply part is connected with an external power supply through a plug stretching out of the base.

According to the novel mouse repeller of the invention, the ultrasonic output part further comprises an MCU square wave output circuit and an ultrasonic power amplification circuit; the MCU square wave output circuit transmits an ultrasonic signal to the ultrasonic power amplification circuit; the negative ion generator further comprises a square wave oscillator and a negative ion circuit board, and the square wave oscillator transmits the signal to the negative ion circuit board.

The novel mouse repeller of the invention is provided with the cavity defined by the shell and the base, and the power rectification and supply part, the ultrasonic output module and the negative ion generator which are located in the cavity, and the ultrasonic transducer of the ultrasonic output module protrudes out of the shell, so that the ultrasonic mouse repelling effect and the negative ion mouse repelling effect are combined, and an integrated structure is formed; compared with a non-integrated structure, the occupied space is reduced, the number of required sockets is reduced, and the using effect in the same area is remarkable; the adopted detachable and cleanable negative ion discharge electrode plate is high in power, when dust on the high-voltage electrode plate affects the negative ion emitting effect, the electrode plate can be detached and cleaned and then reused, so that a powerful negative iron emitting effect is maintained, and the use cost is reduced; the mouse repelling effect is further improved through the ultrasonic transducer, and detachable discharge electrode plate is a negative ion static electrode, so that the service life of the negative ion generator is prolonged, and meanwhile, more negative ions can be emitted.

BRIEF DESCRIPTION OF THE SEVERAL VIEWS OF THE DRAWINGS

A further description of the invention is given with the accompanying drawings and an embodiment as follows, in the drawings.

DETAILED DESCRIPTION OF THE INVENTION

For a better understanding of the purposes, technical schemes and advantages of the invention, a further detailed description of the invention is given with accompanying drawings and embodiment as follows. It should be understood that the specific embodiment in the following description is only used for explaining the invention instead of being used for limiting the invention.

Figure 1:
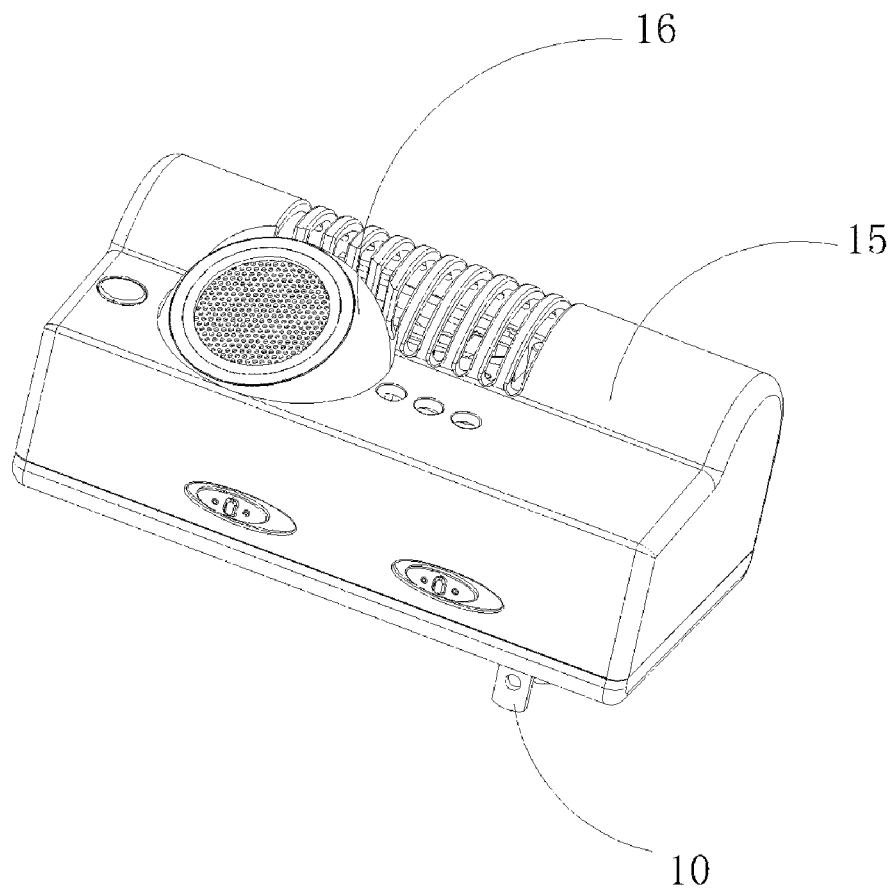
FIG. 1 is an overall appearance diagram of a novel mouse repeller of the invention.
Figure 2:
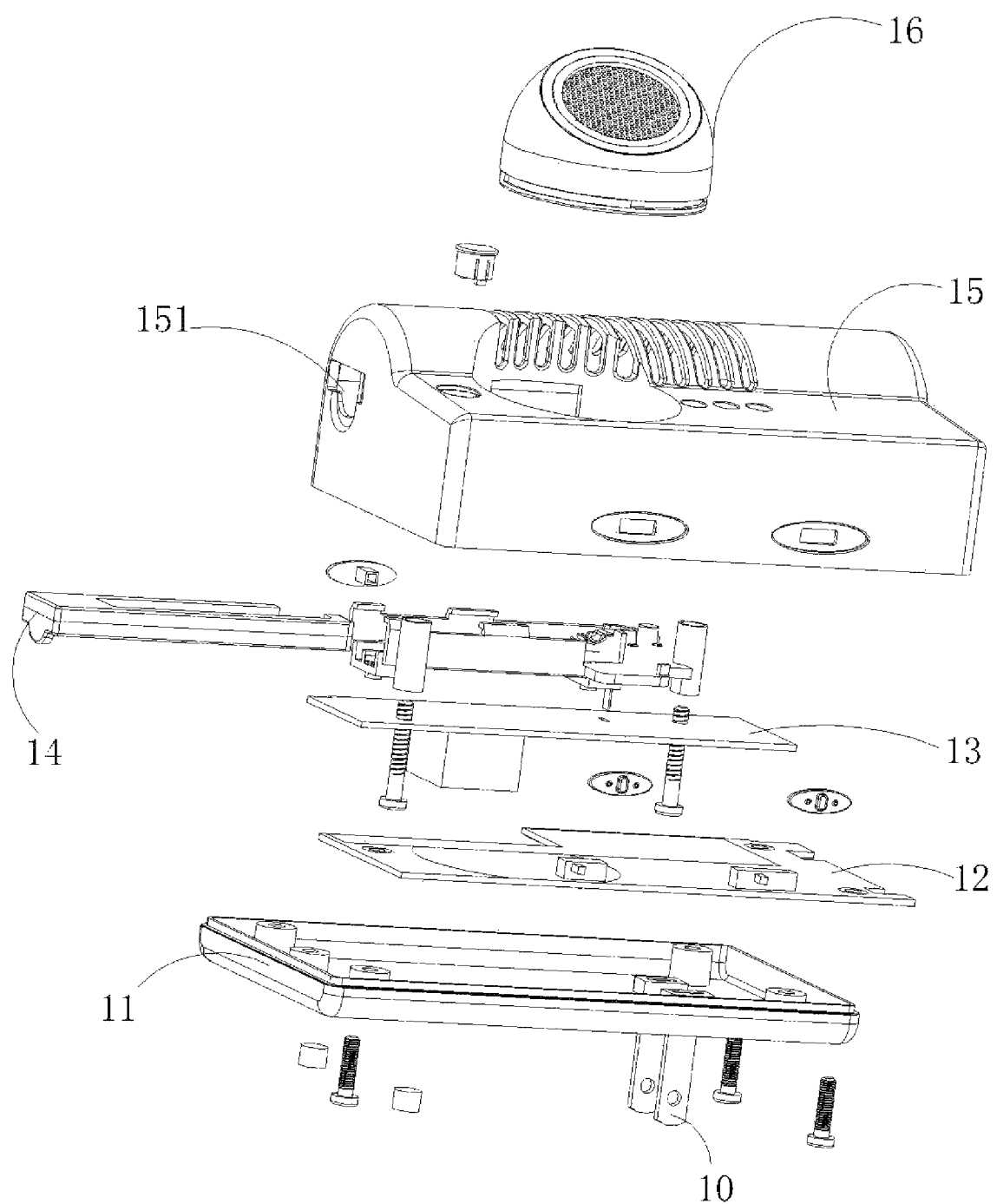
FIG. 2 is an ultrasonic exploded structural diagram of the novel mouse repeller of the invention.
Figure 3:
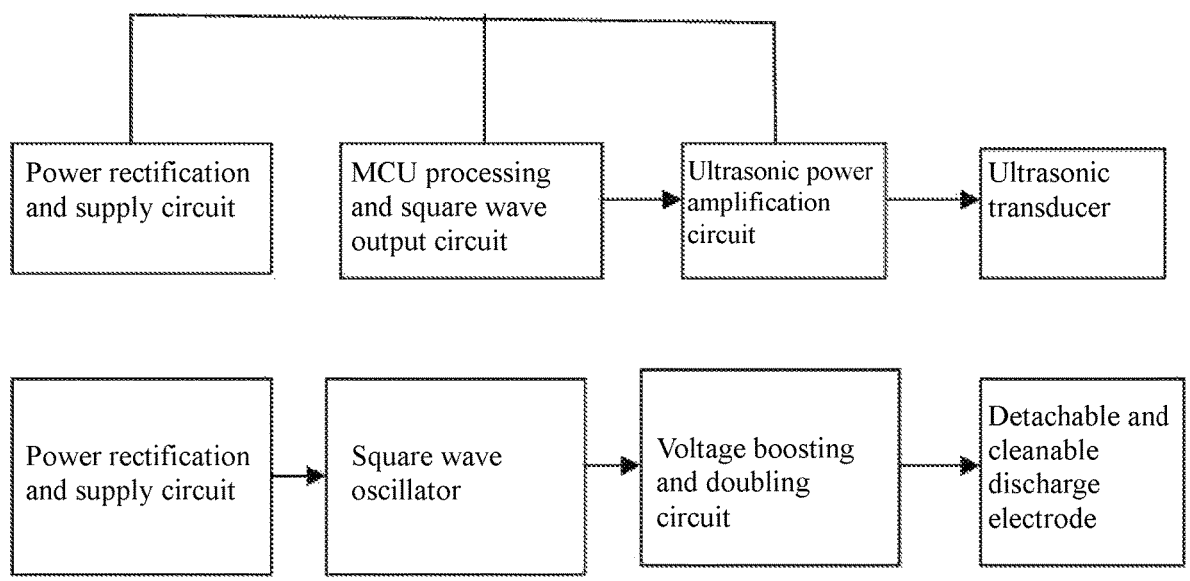
FIG. 3 is a circuit block diagram of the novel mouse repeller of the invention.

As is shown in FIGS. 1-3, a novel mouse repeller comprises a cavity defined by a shell 15 and a base 11, and a power rectification and supply part, an ultrasonic output module and a negative ion generator which are located in the cavity, wherein the power rectification and supply part supplies power to the ultrasonic output module and the negative ion generator, and the ultrasonic output module comprises an MCU square wave output circuit, an ultrasonic power amplification circuit and an ultrasonic transducer 16; in the operating process, the MCU square wave output circuit transmits an ultrasonic signal to the ultrasonic power amplification circuit, the ultrasonic power amplification circuit then transmits the ultrasonic signal to the ultrasonic transducer 16, and thus ultrasonic waves are emitted; the ultrasonic transducer 16 protrudes out of the shell 15 and matched with a hole in the shell 15 in shape, so that the size of the mouse repeller is minimized, and the structure is compact; meanwhile, the ultrasonic output function and the function of the negative ion generator are combined, so that an integrated structure is formed, and the occupied space is reduced; the negative ion generator comprises a square wave oscillator, a negative ion circuit board 13 and a discharge electrode plate 14, and the negative ion circuit board 13 penetrates through the negative ion discharge electrode plate 14 to be connected with the shell 15 through bolts; as is shown in FIG. 3, the square wave oscillator transmits a signal to a voltage boosting and doubling circuit, and then the signal is transmitted to the detachable and cleanable discharge electrode plate, so that negative ions are emitted; the discharge electrode plate 14 is a detachable and cleanable discharge electrode plate and is high in power; when dust on the electrode plate affects the negative ion emitting effect, the electrode plate can be detached and cleaned and then reused, so that a powerful negative iron emitting effect is maintained, and the use cost is reduced. In this way, the mouse repeller is small and exquisite in structure, small in occupied space, remarkable in mouse repelling effect and low in use cost.

Furthermore, as is shown in FIG. 2, the shell 15 is provided with a hole 151 at the end of the discharge electrode plate 14, and thus the discharge electrode plate can be taken, placed and cleaned conveniently; the shape of the hole 151 is matched with the shape of the end face of the discharge electrode plate 14, so that dust in the outside is prevented from entering the electrode plate through the hole, and the influence of the dust in the outside on the performance of the electrode plate is avoided.

Furthermore, the discharge electrode plate 14 is a negative ion static electrode, and compared with a simple carbon brush type negative ion generator, the discharge electrode plate 14 is long in service life and capable of emitting more negative ions, and the mouse repelling effect of the negative ion generator is further improved.

Specifically, as is shown in FIG. 2, the power rectification and supply part is connected with an external power supply through a plug 10 stretching out of the base, and thus the mouse repeller is more compact in overall structure, smaller in size and more convenient to use.

According to the mouse repeller of the invention, the negative ion generator and an ultrasonic mouse repeller are integrated to form an integrated structure, so that the mouse repeller is compact in size, small in occupied space and convenient to use; the mouse repeller repels mice in an area where mice appear frequently by disturbing the audition of the mice with powerful ultrasonic waves, air in the area is made fresh through the negative ion generator so that mice cannot adapt to the environment and then are forced to flee, and under the dual effect of ultrasonic waves and the negative ion generator, the mouse repelling effect is remarkable compared with a single mouse repelling method; meanwhile, the discharge electrode plate of the negative ion generator is a detachable and cleanable electrode plate, so that the use cost is obviously reduced; a static electrode of the negative ion generator is used as the detachable and cleanable electrode plate, so that the service life of the negative ion generator is prolonged; the mouse repeller only occupies the space of one socket.

What needs to be pointed out is that firstly, the mouse repeller of the invention can be used for repelling mice and can also repel ants, cockroaches, spiders, moths and the like; secondly, the mouse repeller of the invention can be used in places such as warehouses, offices, hospitals, supermarkets, hotels and kitchens; thirdly, the effective repelling range of the mouse repeller of the invention can be as wide as 250 square meters.

Although the invention is disclosed through the above embodiment, the protection scope of the invention is not limited to the above embodiment, and transformations, substitutes and the like of the above components made without deviating from the concept of the invention are all within the claim range of the invention.

What is claimed is:

1. A novel mouse repeller, characterized by comprising a cavity defined by a shell and a base, and a power rectification and supply part, an ultrasonic output module and a negative ion generator which are located in the cavity, wherein the power rectification and supply part supplies power to the ultrasonic output module and the negative ion generator, the ultrasonic output module comprises an ultrasonic transducer protruding out of the shell, and the negative iron generator comprises a discharge electrode plate which is a detachable and cleanable electrode plate.

2. The novel mouse repeller according to claim 1, characterized in that the shell is provided with a hole at the end of the discharge electrode plate, and the shape of the hole is matched with the shape of the end face of the discharge electrode plate.

3. The novel mouse repeller according to claim 1, characterized in that the discharge electrode plate is a negative ion static electrode.

4. The novel mouse repeller according to claim 2, characterized in that the discharge electrode plate is a negative ion static electrode.

5. The novel mouse repeller according to claim 3, characterized in that the power rectification and supply part is connected with an external power supply through a plug stretching out of the base.

6. The novel mouse repeller according to claim 4, characterized in that the power rectification and supply part is connected with an external power supply through a plug stretching out of the base.

7. The novel mouse repeller according to claim 5, characterized in that the ultrasonic output part further comprises an MCU square wave output circuit and an ultrasonic power amplification circuit; the MCU square wave output circuit transmits an ultrasonic signal to the ultrasonic power amplification circuit; the negative ion generator further comprises a square wave oscillator and a negative ion circuit board, and the square wave oscillator transmits the signal to the negative ion circuit board.

8. The novel mouse repeller according to claim 6, characterized in that the ultrasonic output part further comprises an MCU square wave output circuit and an ultrasonic power amplification circuit; the MCU square wave output circuit transmits an ultrasonic signal to the ultrasonic power amplification circuit; the negative ion generator further comprises a square wave oscillator and a negative ion circuit board, and the square wave oscillator transmits the signal to the negative ion circuit board.

\* \* \* \* \*